United States Patent
Horton (10) Patent No.: US 11,006,964 B2
(45) Date of Patent: *May 18, 2021

(54) FLEXIBLE INTRA-VASCULAR ANEURYSM TREATMENT STENT

(71) Applicant: Joseph Horton, Birmingham, AL (US)

(72) Inventor: Joseph Horton, Birmingham, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/451,070

(22) Filed: Jun. 25, 2019

(65) Prior Publication Data

US 2019/0307461 A1    Oct. 10, 2019

Related U.S. Application Data (60) Continuation of application No. 15/906,411, filed on Feb. 27, 2018, now Pat. No. 10,327,782, which is a continuation of application No. 15/608,481, filed on May 30, 2017, now Pat. No. 9,901,349, which is a continuation of application No. 15/156,653, filed on May 17, 2016, now Pat. No. 9,662,234, which is a division of application No. 13/839,775, filed on Mar. 15, 2013, now Pat. No. 9,339,400.

(60) Provisional application No. 61/764,920, filed on Feb. 14, 2013.

(51) Int. Cl.
| | | |
|---|---|---|
| A61F 2/88 | (2006.01) | |
| A61B 17/12 | (2006.01) | |
| A61F 2/915 | (2013.01) | |
| A61F 2/82 | (2013.01) | |
| A61B 17/00 | (2006.01) | |

(52) U.S. Cl.
CPC .. *A61B 17/12118* (2013.01); *A61B 17/12145* (2013.01); *A61F 2/88* (2013.01); *A61B 2017/00867* (2013.01); *A61F 2/915* (2013.01); *A61F 2002/823* (2013.01); *A61F 2210/0014* (2013.01); *A61F 2230/0034* (2013.01)

(58) Field of Classification Search
CPC ................................. A61F 2/88; A61B 17/12
See application file for complete search history.

(56) References Cited

U.S. PATENT DOCUMENTS

| | | | |
|---|---|---|---|
| 5,108,417 | A | 4/1992 | Sawyer |
| 5,782,905 | A | 7/1998 | Richter |
| 8,277,500 | B2 | 10/2012 | Schmid et al. |
| 8,409,267 | B2 | 4/2013 | Berez et al. |
| 2004/0193141 | A1 | 9/2004 | Leopold et al. |
| 2006/0195178 | A1 | 8/2006 | West |
| 2006/0271158 | A1 | 11/2006 | Olson |

(Continued)

OTHER PUBLICATIONS

International Search Report dated Dec. 11, 2017 from PCT/US17/53287.

*Primary Examiner* — Matthew W Schall (57) ABSTRACT

An intra-vascular aneurysm-treatment stent and a method for lowering pressure within an aneurysm bubble in a blood vessel. A stent coil is insertable into a blood vessel, the coil made of a material sufficiently flexible to move around curves, loops, and corners in the blood vessel. The stent coil is positioned in the blood vessel with selected stent coil portions proximate an opening into either a saccular aneurysm or a fusiform aneurysm. Blood in the lumen of the blood vessel flows past the leading edges and both over the outer surfaces, and under the inner surfaces. A portion of the blood inside the aneurysm becomes entrained with the blood flowing over the outer surfaces. At the trailing edges, the converging blood flows create eddies.

20 Claims, 6 Drawing Sheets

(56) References Cited

U.S. PATENT DOCUMENTS

| | | |
|---|---|---|
| 2007/0021816 A1 | 1/2007 | Rudin |
| 2008/0306581 A1 | 12/2008 | Berglund et al. |
| 2010/0016950 A1 | 1/2010 | Berglund et al. |
| 2011/0230952 A1 | 9/2011 | Kassab et al. |
| 2011/0276123 A1 | 11/2011 | Davies et al. |
| 2011/0276125 A1 | 11/2011 | Walker et al. |
| 2014/0031920 A1 | 1/2014 | Malek |
| 2014/0228939 A1 | 8/2014 | Horton |
| 2017/0258474 A1 | 9/2017 | Horton |

FLEXIBLE INTRA-VASCULAR ANEURYSM TREATMENT STENT

DESCRIPTION OF THE INVENTION

The present application is a continuation of U.S. application Ser. No. 15/906,411, filed Feb. 27, 2018 (U.S. Pat. No. 10,327,782); which is a continuation of U.S. application Ser. No. 15/608,481, filed May 30, 2017 (U.S. Pat. No. 9,901,349); which is a continuation of U.S. application Ser. No. 15/156,653, filed May 17, 2016 (U.S. Pat. No. 9,662,234); which is a divisional of U.S. application Ser. No. 13/839,775, filed Mar. 15, 2013 (U.S. Pat. No. 9,339,400); which claims the benefit of Provisional Application No. 61/764,920, filed Feb. 14, 2013; all the contents of which are incorporated herein by reference.

FIELD OF THE INVENTION

The present invention relates to flexible intra-vascular stents and to flow diverters and modifiers, and more particularly to flexible wire intra-vascular stents for treatment of aneurysms in the carotid and vertebral arteries and branch blood vessels extending from the carotid and vertebral arteries into the brain.

BACKGROUND OF THE INVENTION

An aneurysm is a circumscribed dilation of a blood vessel, or cardiac chamber, in direct communication with its respective lumen, usually resulting from an acquired or congenital weakness of the wall of the blood vessel, or chamber. An aneurysm occurs when a part of the artery, other blood vessel, or cardiac chamber, swells, either due to damage to the wall or a weakness in the wall. As blood pressure builds up with each heartbeat, the wall balloons out at its weakest point, forming an aneurysm bubble. The bubble tends to fill with blood, as blood flowing through the lumen is partly diverted through the opening into the aneurysm. As the aneurysm grows, in addition to causing pain and other complications, a risk of rupture of the bubble increases. Rupture of an aneurysm in a carotid or vertebral artery in the neck, or in a branch blood vessel extending from the carotid or vertebral artery into the brain can cause a hemorrhage or stroke, which can be at best severely debilitating, and at worst deadly. For perspective, aneurysmal subarachnoid hemorrhage (SAH) occurs about 30,000 times annually in the United States. Of these, between ⅓ and ½ of those so afflicted will not survive the trip to the hospital.

Figure 1:
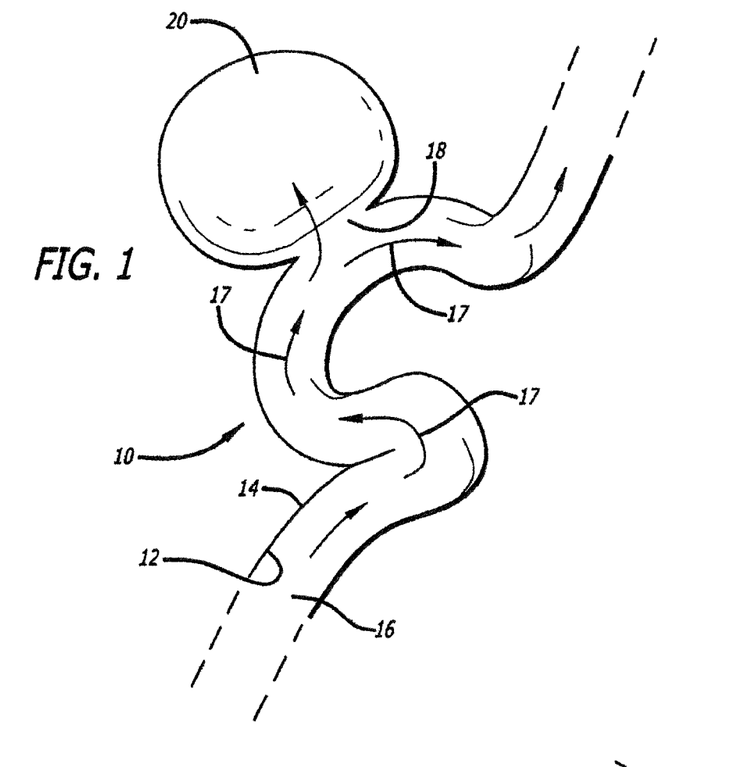
FIG. 1 is a side view of a blood vessel, with a saccular aneurysm located on one outer surface of the blood vessel.
Figure 2:
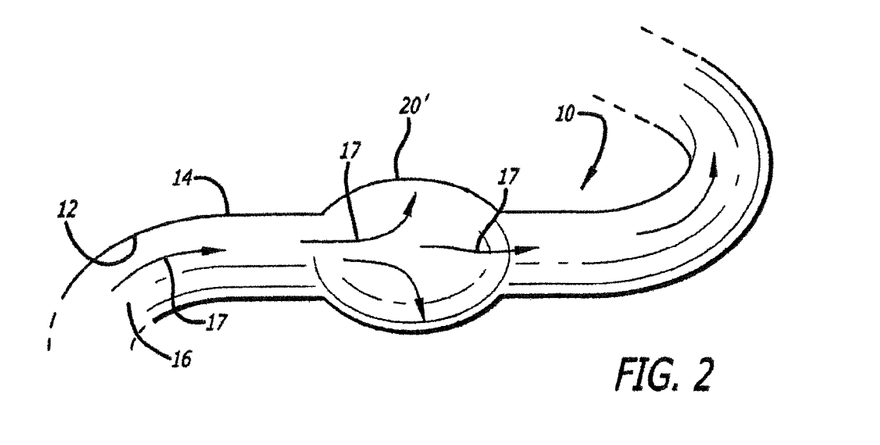
FIG. 2 is a side view of a blood vessel with a fusiform aneurysm, defined by a circumferential dilatation of the artery.

FIGS. 1 and 2 depict various configurations of aneurysms. In each drawing, a generally tubular blood vessel 10 comprises an inner peripheral wall 12, and an outer peripheral wall 14. The inner peripheral wall 12 defines a lumen 16 through which blood 17 flows. A weak point in the wall 12 has an opening, called a neck, 18. A portion of the blood flow 17 is diverted from the lumen 16 through the neck 18 to form and maintain a saccular aneurysm 20. A saccular aneurysm 20 is shown in FIG. 1. FIG. 2 shows a fusiform aneurysm 20'. If the arterial wall weakness is focal, i.e., it does not extend all the way around the artery, the aneurysm is most likely to be saccular. If the weakness is circumferential, it will more likely be fusiform. In the saccular aneurysm 20, its communication with the lumen 16 is though the aneurysm neck 18. The fusiform aneurysm 20' by definition does not have a neck.

Figure 3A:
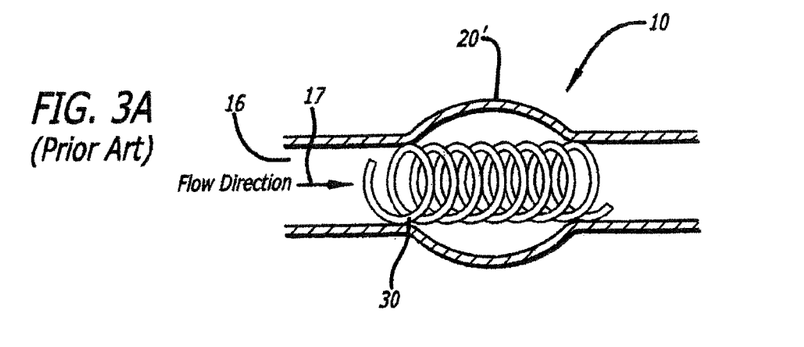
FIG. 3A is a perspective view of a coil stent in a blood vessel, used in a conventional attempt to treat a fusiform aneurysm.
Figure 3B:
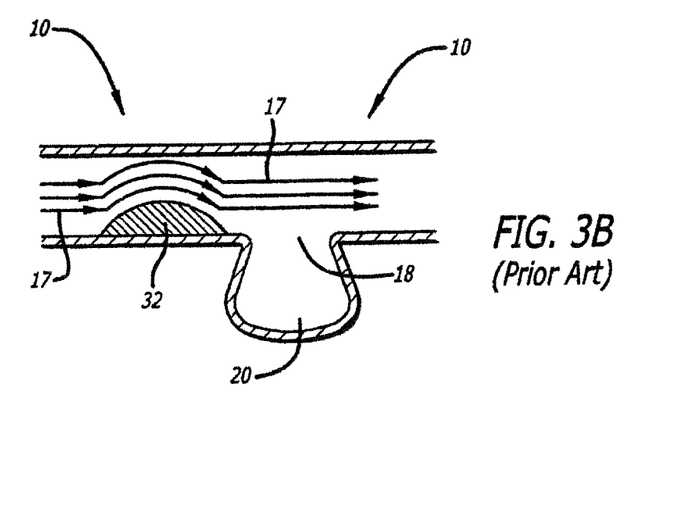
FIG. 3B depicts a conventional attempt to treat an aneurism, using the coil stent of FIG. 3A.

FIGS. 3A-3B depict a conventional attempt to treat aneurysms. FIG. 3A depicts a wire stent 30, installed in a blood vessel 10 with a fusiform aneurysm bubble 20'. Referring to FIG. 3B, a raised strut portion 32 of the wire stent 30 depicted in FIG. 3A is provided against the blood vessel inner peripheral wall 12 immediately upstream of the aneurysm neck 18. It is intended that an increase in velocity of the blood flow 17 over the raised strut portion 32 will create a pressure drop (dP) at a trailing edge thereof to cause blood 17 in the saccular aneurysm bubble 20 to flow back into the lumen 16 of the blood vessel 10.

Figure 4:
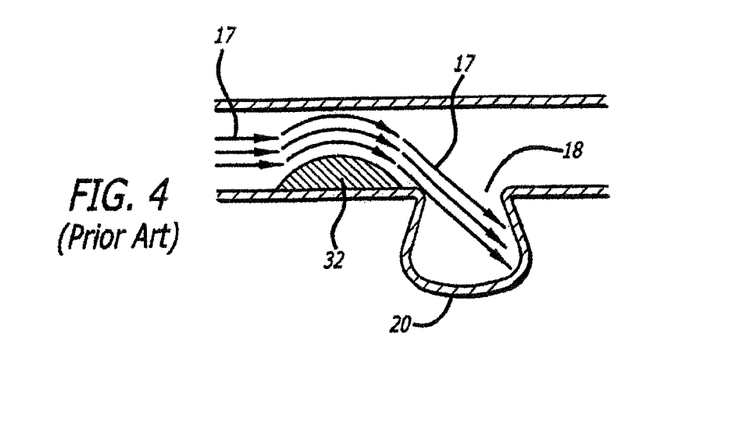
FIG. 4 is a side schematic view depicting the operation of the conventional attempt to treat aneurysms depicted in FIG. 3B, and demonstrating why the conventional attempt is sometimes ineffective.
Figure 5:
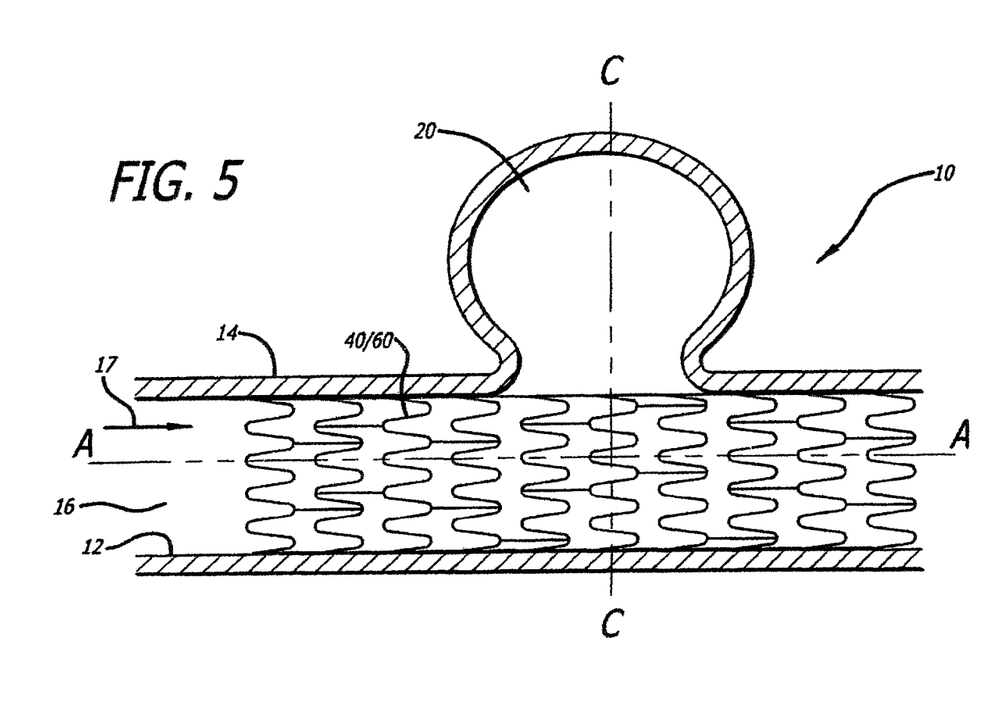
FIG. 5 is a side view of a flexible intra-vascular stent, in accordance with the invention, positioned in a blood vessel proximate an aneurysm.

FIG. 4 explains why this conventional attempt to treat aneurysms is sometimes ineffective, even harmful. At the trailing edge of the raised strut portion 32, as in the case of a trailing edge of an airplane, the flow of fluid (in this case blood 17) flows across the apex of the wing and down past the trailing edge. The configuration and positioning of the strut 32 in FIG. 3B, however, rather than creating a pressure drop (dP), drawing blood 17 out of the saccular aneurysm 20 and into the lumen 16, instead directs more blood flow 17 at the trailing edge into the saccular aneurysm 20, thereby achieving an effect opposite of that which was intended. In fact, it can have the effect of directing high-velocity blood to strike the inflow zone of the aneurysm, a fragile, delicate part.

SUMMARY OF THE INVENTION

In accordance with the invention, a flexible intra-vascular catheter for treating an aneurysm includes an expanding coil insertable into a blood vessel, including a curving blood vessel, with coil portions positioned proximate an opening in the blood vessel wall into an aneurysm bubble, the coil portions are configured to receive blood flow in the blood vessel on their upstream side/leading edge and re-direct the blood flow back toward a central lumen of the blood vessel, thereby creating an eddy effect proximate the downstream side/trailing edge of the respective coil portions, creating a pressure drop (dP) which draws blood in the aneurysm bubble back into the lumen of the blood vessel, and collapsing the bubble, or at least substantially decreasing pressure in it.

In one embodiment, the coil portions have an arcuate upper surface proximate the inner blood vessel wall and facing the opening into the aneurysm bubble, and generally flat inner surfaces facing the lumen of the blood vessel. Blood flow on the upstream side/leading edge of each coil portion travels over and across the arcuate outer surface and is directed back down toward the lumen of the blood vessel. Proximate the opening into the aneurysm bubble, on the downstream side/trailing edge of each coil portion, this downward flow converges with the flow along the flat inner surfaces, creating an eddy, with a corresponding pressure drop (dP). The dP draws blood out of the aneurysm bubble and back into the lumen of the blood vessel, thereby collapsing the bubble, or decreasing pressure in it.

In another embodiment, the coil portions have convex outer surfaces proximate the inner wall of the blood vessel and facing the opening into the aneurysm bubble, and concave inner surfaces facing the lumen of the blood vessel. Blood flow from upstream flows over and across each convex outer surface, and also flows into each successive concave inner surface at its respective upstream/leading edge portion, and out of the concave inner face at its respective trailing edge, being redirected back toward the lumen of the blood vessel. The converging blood flows at each respective downstream/trailing edge portion, create an eddy at each downstream/trailing edge portion. Once again, each eddy creates a corresponding pressure drop dP. This dP draws blood out of the aneurysm bubble and toward the lumen of the blood vessel, thereby collapsing the bubble, or decreasing pressure in it.

The accompanying drawings, which are incorporated in and constitute a part of this specification, illustrate preferred embodiments of the invention and together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

As broadly embodied herein, referring to FIGS. 5-8B, a flexible coil intra-vascular stent 40/60 in accordance with the invention comprises a self-expanding or balloon-expanded generally tubular stent, flexible for going around curves, loops, and corners in blood vessels, particularly carotid or vertebral arteries in the neck, and branch blood vessels leading off the carotid arteries into the brain. It is preferred that the stent 40/60 be made of flexible wire, which in a preferred embodiment is formed of a memory metal such as Nitinol. In another preferred embodiment the stent 40/60 is formed of a non-memory metal, e.g., stainless steel.

Preferred configurations and operation of the flexible intra-vascular wire stent 40/60 in accordance with the invention is explained with respect to FIGS. 6A-7C.

Figure 6A:
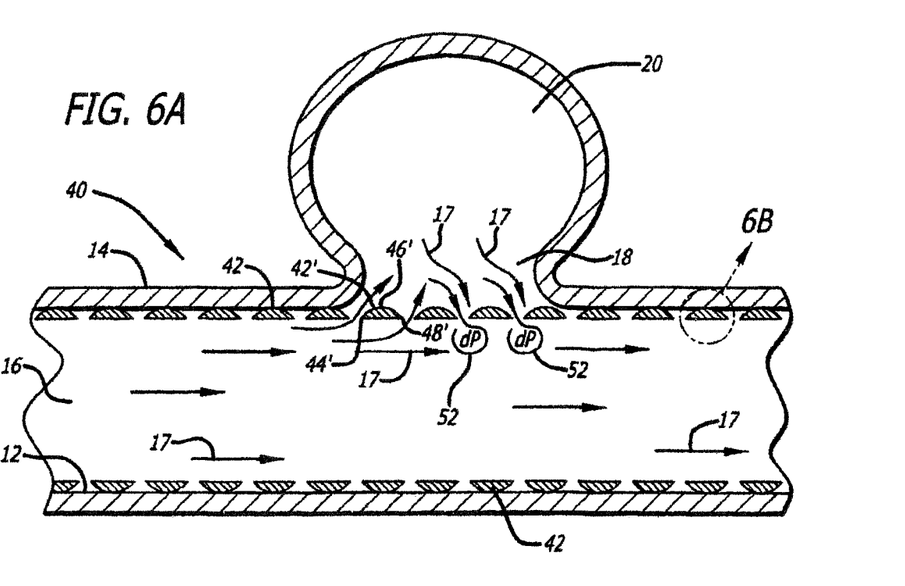
FIG. 6A is a side cross-sectional view of a first embodiment of the flexible intra-vascular stent of FIG. 5, positioned in a blood vessel proximate an aneurysm.

As broadly embodied in FIG. 6A, a first embodiment of a flexible intra-vascular wire coil stent 40 is positioned in a generally tubular blood vessel 10, the blood vessel 10 including a peripheral inner wall 12, a peripheral outer wall 14, a central lumen 16, and an aneurysm neck 18 in the wall 12, allowing blood 17 to flow from the lumen 16 into an aneurysm bubble 20.

Figures 6B, 6C:
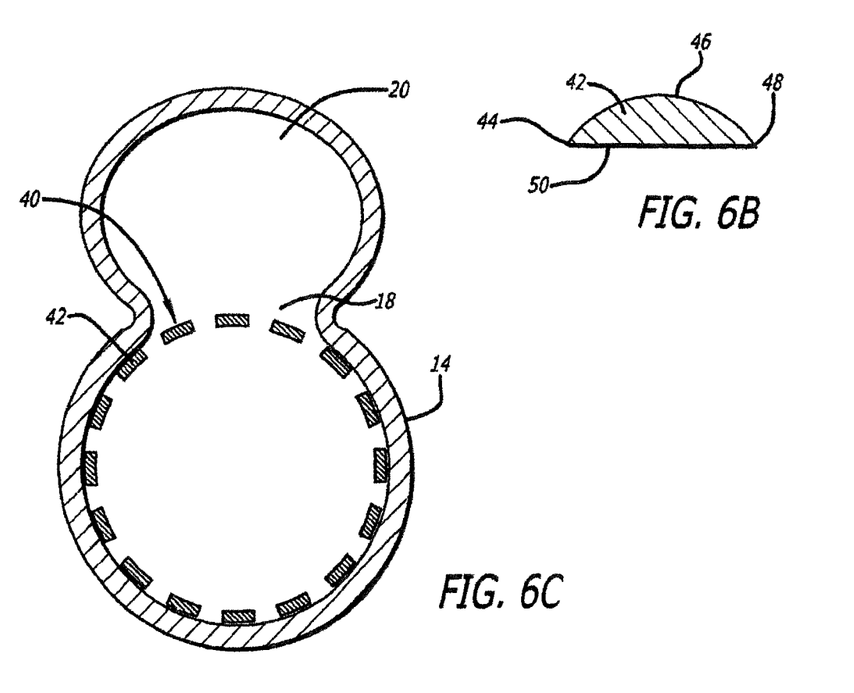
FIG. 6B is a side cross-sectional view of one coil portion of the first embodiment of the flexible intra-vascular stent of FIG. 6A.
FIG. 6C is an cross-sectional end view of the flexible intra-vascular stent of FIG. 6A, positioned in a blood vessel proximate an aneurysm.

Flexible intra-vascular wire coil stent 40 includes a plurality of sequential coil portions 42, depicted in cross-section in FIGS. 6A and 6B. As depicted in FIGS. 6A and 6B, each coil portion 42 includes an upstream leading edge 44, an outer surface 46, a downstream trailing edge 48, and an inner surface 50. Each outer surface 46 defines an arc between the leading edge 44 and the trailing edge 48, whereas the inner surface 50 is substantially flat. Moreover, whereas several of the outer surfaces 46 face the inner wall 12 of the blood vessel 10, and the inner surfaces 50 all face the lumen 16 of the blood vessel 12, selected coil portions 42' have outer portions 46' facing the neck 18 into the aneurysm 20.

In operation, blood flow 17 in the lumen 16 will flow past the generally flat inner surfaces 50, with some blood flow 17 being diverted by the leading edges 44' of the selected coil portions 42' facing the neck 18, across the outer surfaces 46', past the trailing edges 48' and back towards the lumen 16. Comparing FIG. 6A to FIG. 4, it can be seen that rather than directing blood flow into the aneurysm 20, as was the case with the conventional art, selected coil portions 42' direct blood flow away from the aneurysm 20 and toward the lumen 16. Some of the blood 17 in the aneurysm 20 will become entrained in the blood flow 17 over the outer surfaces 46' and be directed back into the lumen 16. More significantly, the converging blood flow paths 17 at the trailing edges 48' of the selected coil portions 42' create eddies 52 proximate the trailing edges 48' of the selected coil portions 42'. Each eddy 52 results in a pressure drop dP between pressure at the respective outer surface 46' and the respective trailing edge 48'. The dP generated at the respective trailing edges 48' will draw blood 17 out of the aneurysm 20 and back into the blood flow 17 in the lumen 16, thereby collapsing the bubble 20, or at least decreasing it.

Figure 7A:
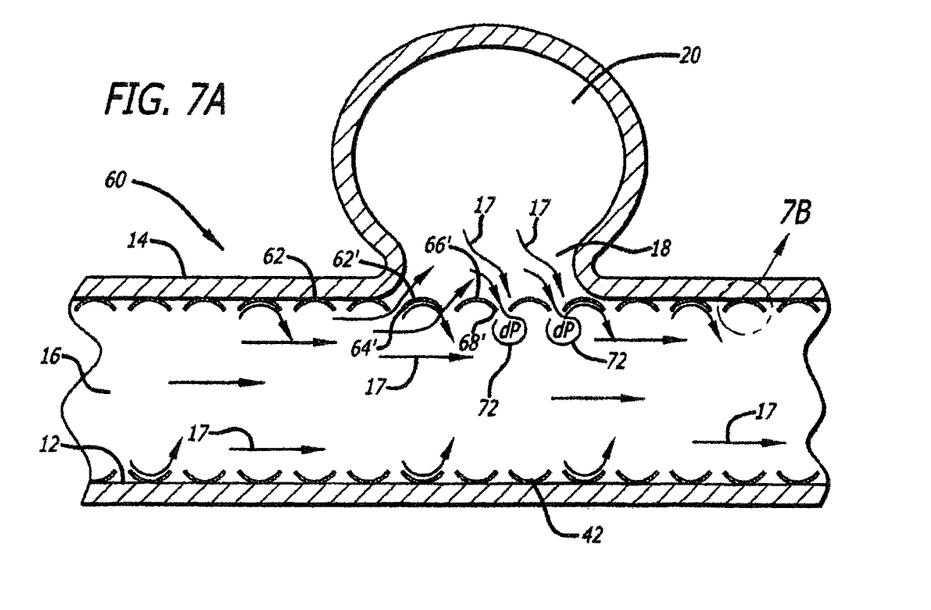
FIG. 7A is a side view of a second embodiment of the flexible intra-vascular stent of FIG. 5, positioned in a blood vessel proximate an aneurysm.
Figures 7B, 7C:
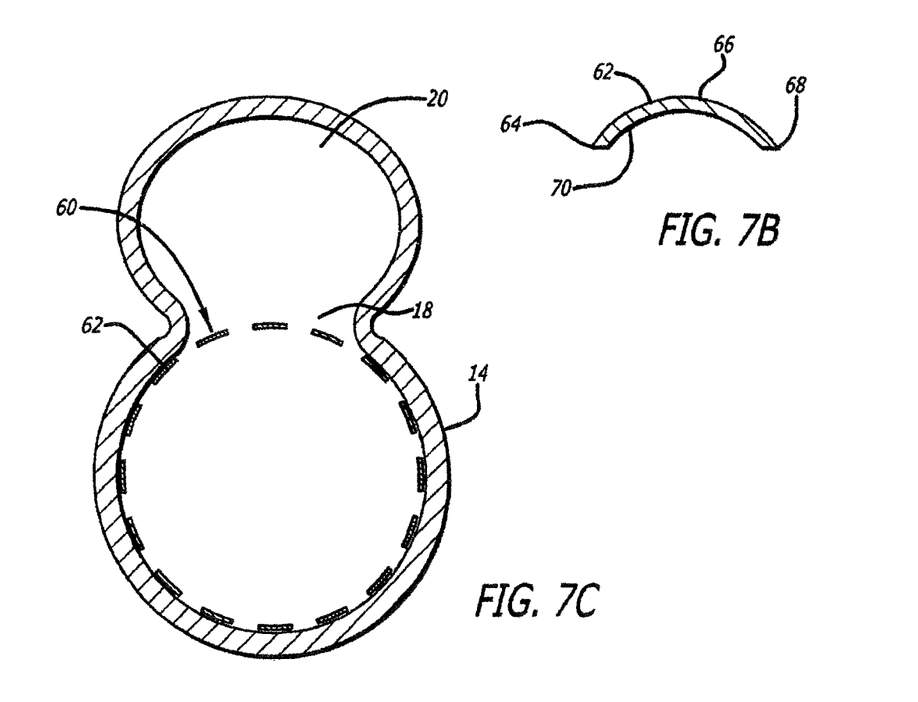
FIG. 7B is a cross-sectional end view of one coil portion of the second embodiment of the flexible intra-vascular stent of FIG. 7A.
FIG. 7C is an cross-sectional end view of the flexible intra-vascular stent of FIG. 7A, positioned in a blood vessel proximate an aneurysm.
Figure 8A:
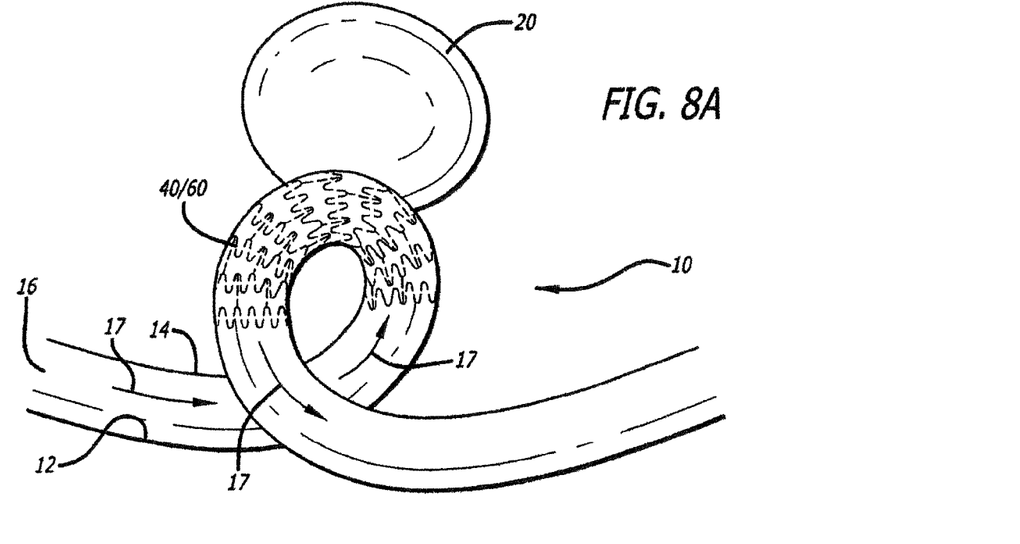
FIG. 8A is a side view of a blood vessel with a loop defined therein, an aneurysm positioned on a wall of the loop, and the flexible intra-vascular stent of FIG. 5 positioned in the loop proximate the aneurysm.
Figure 8B:
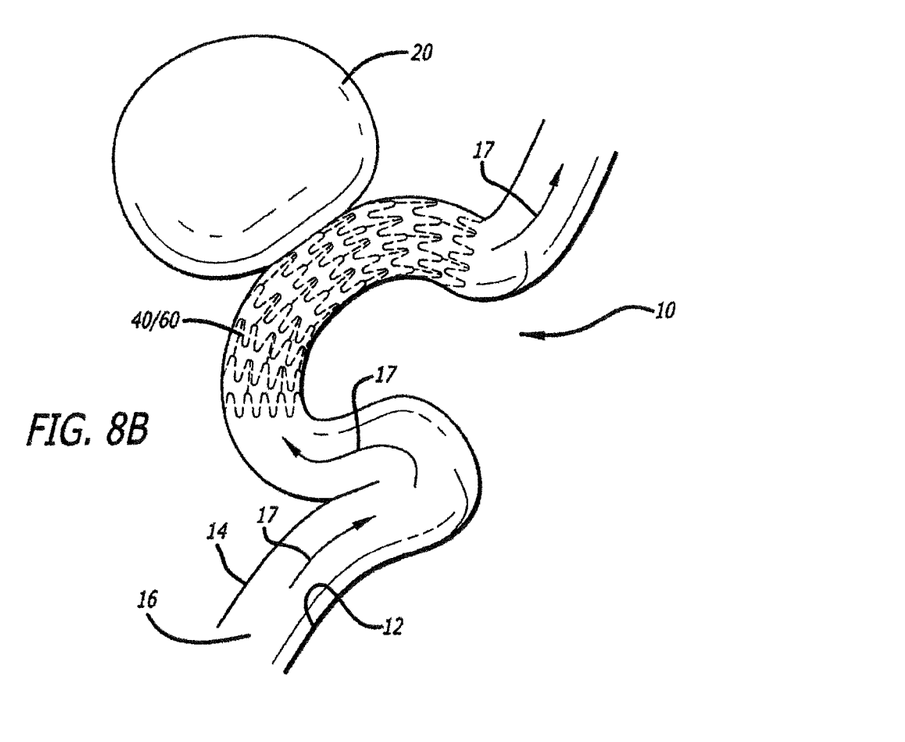
FIG. 8B is a side view of a curved blood vessel, with an aneurysm positioned on a wall of the curve, and the flexible intra-vascular stent of FIG. 5 positioned in the curve proximate the aneurysm.

In the second embodiment, as depicted in FIGS. 7A and 7B, each coil portion 62 of a flexible wire coil intra-vascular stent 60 includes an upstream leading edge 64, an outer surface 66, a downstream trailing edge 68, and an inner surface 70. In the second embodiment of FIGS. 7A and 7B, the outer surface 66 defines a convex surface between the leading edge 64 and the trailing edge 68, whereas the inner surface 70 defines a concave surface between the leading edge 64 and the trailing edge 68. Moreover, whereas several of the outer surfaces 66 face the inner wall 12 of the blood vessel 10, and the inner surfaces 70 all face the lumen 16 of the blood vessel 10, selected coil portions 62' have outer surfaces 66' facing the neck 18 into the aneurysm 20.

In operation, blood flow 17 in the lumen 16 will flow into and out of the concave inner surfaces 70, with some blood flow 17 being diverted by the leading edges 64' of the selected coil portions 62' proximate the neck 18, across the convex outer surfaces 66', past the trailing edges 68' and back towards the lumen 16. As discussed above with respect to the embodiment of FIG. 6A, some of the blood 17 in the aneurysm 20 will become entrained in the blood flow 17 passing across the outer surfaces 66' and will flow back into the lumen 16. More significantly, the converging blood flow paths 17 at the selected trailing edges 68' create eddies 72 proximate the trailing edges 68' of the selected coil portions 62', each eddy 72 resulting in a pressure drop dP between pressure at the respective convex outer surface 66' and the respective trailing edge 68'. In the location of the selected coil portions 62', the dP generated at the respective trailing edges 68' will draw blood 17 out of the aneurysm 20 and back into the blood flow 17 in the lumen 16, thereby collapsing the bubble 20, or at least decreasing it.

What is claimed is:

1. A method for flowing blood from of an aneurysm bubble in a blood vessel back into the blood vessel, the method comprising:

utilizing an intravascular stent having an upstream proximal end, an opposite downstream distal end, a length between the proximal end and the distal end, and a longitudinal axis along the length, the stent having selected stent portions with leading edges directed toward the proximal end, trailing edges directed toward the distal end, outer surfaces, and inner surfaces, each of the outer surfaces having a first length between the leading edge and the trailing edge, each of the inner surfaces having a leading edge, a trailing edge, and a second length between the leading edge of the inner surface and the trailing edge of the inner surface, the first length being greater than the second length, the first length and the second length being measured in a plane parallel to the longitudinal axis of the stent;

inserting the stent into the blood vessel, with the selected stent portions positioned adjacent an opening into the aneurysm bubble; and flowing blood through the blood vessel and the stent, with first blood flow portions flowing in first paths past the inner surfaces of the selected stent portions and second blood flow portions diverted by the leading edges of the selected stent portions to flow in second paths over the outer surfaces and past the trailing edges of the selected stent portions, the flow of the second blood flow portions over the outer surfaces entraining therein at least a portion of an amount of blood flow in the aneurysm bubble, the second blood flow portions converging with the first blood flow portions at the respective trailing edges of the selected stent portions, the converging first and second blood flow portions directing blood away from the aneurysm bubble and back into the blood vessel.

2. The method of claim 1, wherein inserting the stent further comprises inserting a flexible stent made of a memory material around curves, loops, and corners in blood vessels.

3. The method of claim 1, wherein inserting the stent further comprises inserting a flexible stent made of a non-memory material around curves, loops, and corners in blood vessels.

4. The method of claim 1, wherein the stent is configured as a coil, and the stent portions are configured as coil portions.

5. The method of claim 1, wherein the stent is configured as an expanding generally tubular stent.

6. The method of claim 5, where in the expanding generally tubular stent is one of the group consisting of a self-expanding generally tubular stent, and a balloon expanded generally tubular stent.

7. The method of claim 1, wherein the outer surfaces are substantially arcuate surfaces.

8. The method of claim 1, wherein the outer surfaces have a convex configuration.

9. The method of claim 1, wherein the inner surfaces are substantially planar surfaces extending from the leading edges of the inner surface to proximate the trailing edges of the inner surface.

10. The method of claim 1, wherein the inner surfaces are concave surfaces positioned in a plane substantially parallel to the longitudinal axis and extending from the leading edges of the inner surface to proximate the trailing edges of the inner surface.

11. A method for flowing blood from of an aneurysm bubble in a blood vessel back into the blood vessel, the method comprising:

utilizing an intravascular stent having an upstream proximal end, an opposite downstream distal end, a length between the proximal end and the distal end, and a longitudinal axis along the length, the stent having selected stent portions with leading edges directed toward the proximal end, trailing edges directed toward the distal end, outer surfaces, and inner surfaces, each of the outer surfaces having a first length between the leading edge of the selected stent portions and the trailing edge of the selected stent portions, each of the inner surfaces having a leading edge, a trailing edge, and a second length between the leading edge of the inner surface and the trailing edge of the inner surface;

inserting the stent into the blood vessel, with the selected stent portions positioned adjacent an opening into the aneurysm bubble;

flowing blood through the blood vessel and the stent, with first blood flow portions flowing in first paths past the inner surfaces of the selected stent portions and second blood flow portions diverted by the leading edges of the selected stent portions to flow in second paths over the outer surfaces and past the trailing edges of the selected stent portions, the velocity of the flow of the second blood flow portions over the outer surfaces being greater than the velocity of the flow of the first blood flow portions past the inner surface, the flow of the second blood flow portions over the outer surfaces entraining therein at least a portion of an amount of blood flow in the aneurysm bubble, the second blood flow portions converging with the first blood flow portions at the respective trailing edges of the selected stent portions, the converging first and second blood flow portions directing blood away from the aneurysm bubble and back into the blood vessel.

12. The method of claim 11, wherein inserting the stent further comprises inserting a flexible stent made of a memory material around curves, loops, and corners in blood vessels.

13. The method of claim 11, wherein inserting the stent further comprises inserting a flexible stent made of a non-memory material around curves, loops, and corners in blood vessels.

14. The method of claim 11, wherein the stent is configured as a coil, and the stent portions are configured as coil portions.

15. The method of claim 11, wherein the stent is configured as an expanding generally tubular stent.

16. The method of claim 11, wherein the outer surfaces are substantially arcuate surfaces.

17. The method of claim 11, wherein the outer surfaces have a convex configuration.

18. The method of claim 11, wherein the inner surfaces are substantially planar surfaces extending from the leading edges of the inner surface to proximate the trailing edges of the inner surface.

19. The method of claim 11, wherein the inner surfaces are concave surfaces positioned in a plane substantially parallel to the longitudinal axis and extending from the leading edges of the inner surface to proximate the trailing edges of the inner surface.

20. A method for flowing blood from of an aneurysm bubble in a blood vessel back into the blood vessel, the method comprising:

utilizing an intravascular stent having selected stent portions with leading edges directed toward a proximal end, trailing edges directed toward a distal end, outer surfaces, and inner surfaces, each of the outer surfaces having a first length between the leading edge and the trailing edge, each of the inner surfaces having a leading edge, a trailing edge, and a second length between the leading edge of the inner surface and the trailing edge of the inner surface;

inserting the stent into the blood vessel, with the selected stent portions positioned adjacent an opening into the aneurysm bubble;

flowing blood through the blood vessel and the stent, with first blood flow portions flowing in first paths past the inner surfaces of the selected stent portions;

diverting second blood flow portions via the leading edges of the selected stent portions to flow in second paths over the outer surfaces and past the trailing edges of the selected stent portions, the velocity of the flow of the second blood flow portions over the outer surfaces being greater than the velocity of the flow of the first blood flow portions past the inner surface;

entraining within the flow of the second blood flow portions at least a portion of an amount of blood flow in the aneurysm bubble;

converging the second blood flow portions with the first blood flow portions at the respective trailing edges of the selected stent portions, the converging first and second blood flow portions directing blood away from the aneurysm bubble and back into the blood vessel.

\* \* \* \* \*